United States Patent [19]

Renner et al.

[11] Patent Number: 5,428,659
[45] Date of Patent: Jun. 27, 1995

[54] DEVICE FOR TRANSFERRING ELECTRICAL SIGNALS AND ELECTRIC ENERGY TO THE MEMORY DEVICE OF A CASSETTE

[75] Inventors: Meinrad Renner, Esslingen; Ulrich Barthold, Hohengehren, both of Germany

[73] Assignee: Eastman Kodak Company, Rochester, N.Y.

[21] Appl. No.: 321,385

[22] Filed: Oct. 11, 1994

Related U.S. Application Data

[63] Continuation of Ser. No. 31,422, Mar. 15, 1993, abandoned.

[30] Foreign Application Priority Data

Mar. 16, 1992 [DE] Germany ............... 42 08 347.8

[51] Int. Cl.⁶ .................................... H05G 1/28
[52] U.S. Cl. .......................... 378/162; 378/167
[58] Field of Search ................... 378/162–166; 250/581–590

[56] References Cited

U.S. PATENT DOCUMENTS 4,796,183 1/1989 Ermert et al. ................. 378/15

Primary Examiner—Craig E. Church
Attorney, Agent, or Firm—William F. Noval

[57] ABSTRACT

A device is disclosed for transferring electrical signals and electric energy to a data memory (6) of a cassette (1) for radiation-sensitive recording material (11), the memory being connectable to a signal processing unit (4) and a power source (5) of a cassette identification apparatus (2). Means are provided between cassette (1) and cassette identification apparatus (2) for radio-frequency and galvanically insulated transfer of the signals and the electric energy. Such means feature a coupling device (3) having capacitive, inductive or opto-electric coupling elements that are resistant to corrosion, soiling and wear. Furthermore, the means comprise a signal processing unit (4) having signal transmitter circuits (41, 42, 43) and signal receiver circuits (44, 45, 46) for radio-frequency signals, and a power source (5) having an energy transmitter circuit (52) and an energy receiver circuit (53) for a radio-frequency voltage. The signal processing unit (4) is provided with a microprocessor-controlled CPU (40) for producing and processing the signals, and the energy transmitter circuit (52) features an oscillator circuit (51) for producing the radio-frequency voltage, said oscillator circuit being controllable by means of the signals emitted by the CPU. The energy receiver circuit (53) comprises a signal separating circuit (54) to produce a signal for activating the memory (6).

20 Claims, 6 Drawing Sheets

DEVICE FOR TRANSFERRING ELECTRICAL SIGNALS AND ELECTRIC ENERGY TO THE MEMORY DEVICE OF A CASSETTE

This is a Continuation of application Ser. No. 031,422, filed 15 Mar. 1993 now abandoned.

FIELD OF THE INVENTION

The invention relates to a device for transferring electrical signals and electric energy to a memory of a cassette used for handling radiation-sensitive material, the memory being connectable to a signal processing unit and a power source of a cassette identification apparatus.

BACKGROUND OF THE INVENTION

Devices for transferring electrical signals and electric energy used in cassettes and processing apparatus for radiation-sensitive recording material are known.

From DE-OS 37 31 204 or EP-AP 0307760 an X-ray cassette and a cassette identification apparatus are known to transfer electric energy and electrical signals. Fixed to the X-ray cassette is a memory, in particular a semi-conductor memory (EEPROM), for storing data referring to the patient, the recording material and the cassette. The memory can be connected to a data entry, retrieval and erase section and a power source of the cassette identification apparatus.

It is the object of the invention to provide a device of the generic type having a simple, sturdy and compact structure, in particular a coupling means which is resistant to corrosion, soiling and wear.

The cassette holding radiation-sensitive recording material should also offer safe and easy handling with respect to a cassette identification apparatus and particularly the memory should be protected against loss of data caused by electrostatic charges when handling the cassette and interfering pulses produced by the cassette identification apparatus.

Moreover, a low-loss transfer of both signals and energy at a high transfer rate should be guaranteed.

SUMMARY OF THE INVENTION

According to the invention, the above object is attained in that the device comprises means using radio-frequency for the galvanically insulated transfer of signals and energy.

In an advantageous embodiment of the invention these means comprise a coupling device having capacitive, inductive or opto-electric/electro-optical coupling elements.

Expediently, the means comprise a signal-processing unit having at least one signal transmitter circuit and one signal receiver circuit for radio-frequency signals as well as a power unit having an energy transmitter circuit and an energy receiver circuit for radio-frequency voltage.

The invention also provides for the capacitive coupling element to be provided with a capacitively conducting layer galvanically insulating a contact element of the cassette identification apparatus from a contact element of the cassette, or for the inductive coupling element to be provided with a first induction coil on the cassette identification apparatus galvanically insulated from a second induction coil on the cassette, or for the opto-electric coupling element to be provided with an electro-optical transmitter on the cassette identification apparatus galvanically insulated from an opto-electric receiver on the cassette or vice-versa.

Advantageously, the signal processing unit comprises a microprocessor-controlled central processing unit (CPU) for producing and processing the radio-frequency signals, and the energy transmitter circuit comprises an oscillator circuit for producing a radio-frequency voltage controlled by means of signals emitted by the CPU.

Furthermore, the energy receiver circuit comprises a signal separating circuit for a signal to control the memory which signals superpose the radio-frequency voltage, and protection circuits are provided against interfering pulses in the signal receiver circuits and in the energy transmitter circuit.

Expediently, the dimensions of the coupling device and the power unit are adapted to the radio-frequency selected and the energy level to be transferred.

DESCRIPTION OF THE DRAWINGS

Further features and advantages will be apparent from the description of an embodiment according to the invention shown in the drawing and from the subclaims.

DETAILED DESCRIPTION

Figure 1:
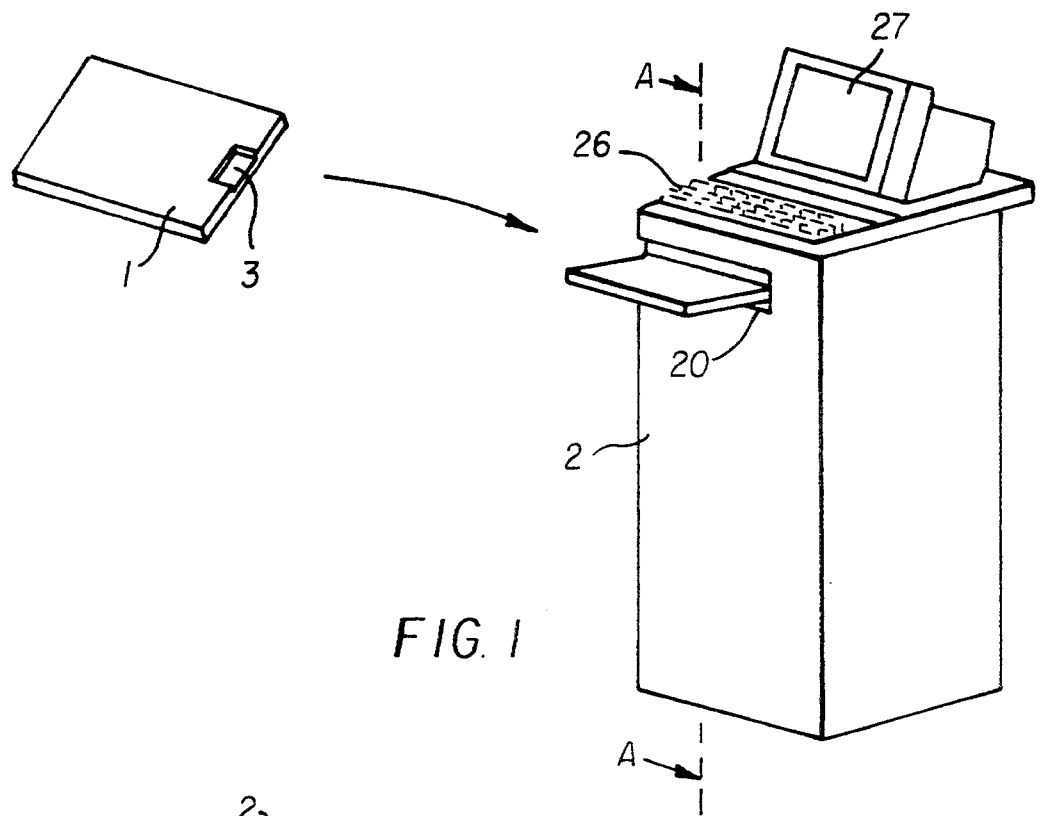
FIG. 1 shows a perspective view of a cassette and a cassette identification apparatus using the device according to the invention.
Figure 2:
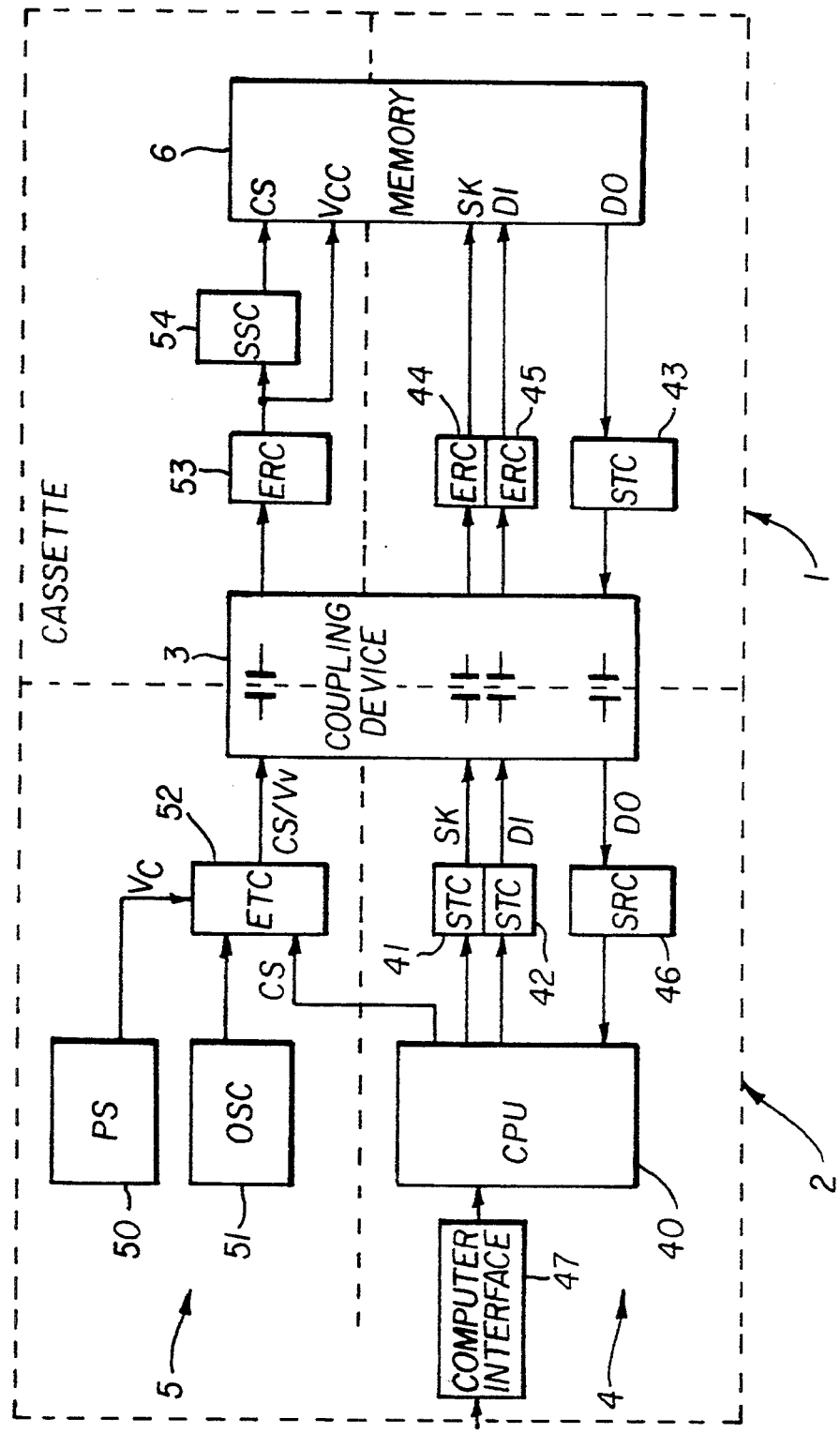
FIG. 2 shows a block diagram of the device according to the invention.

The device shown in FIG. 2 arranged in a cassette identification apparatus 2 and in a cassette 1 according to FIG. 1 comprises a signal processing unit 4, a power source 5 and a capacitive coupling device 3.

On the side of the cassette identification apparatus 2 the signal processing unit comprises signal transmitter circuits 41,42, a signal receiver circuit 46, a CPU 40 and a computer interface 47 (not illustrated), and on the side of the cassette 1 a signal transmitter circuit 43, signal receiver circuits 44,45 and a memory 6.

On the side of the cassette identification apparatus the power source 5 comprises a power unit 50, a radio-frequency oscillator circuit 51 and an energy transmitter circuit 52, and on the side of the cassette an energy receiver circuit 53 and a signal separating circuit 54.

Figure 3:
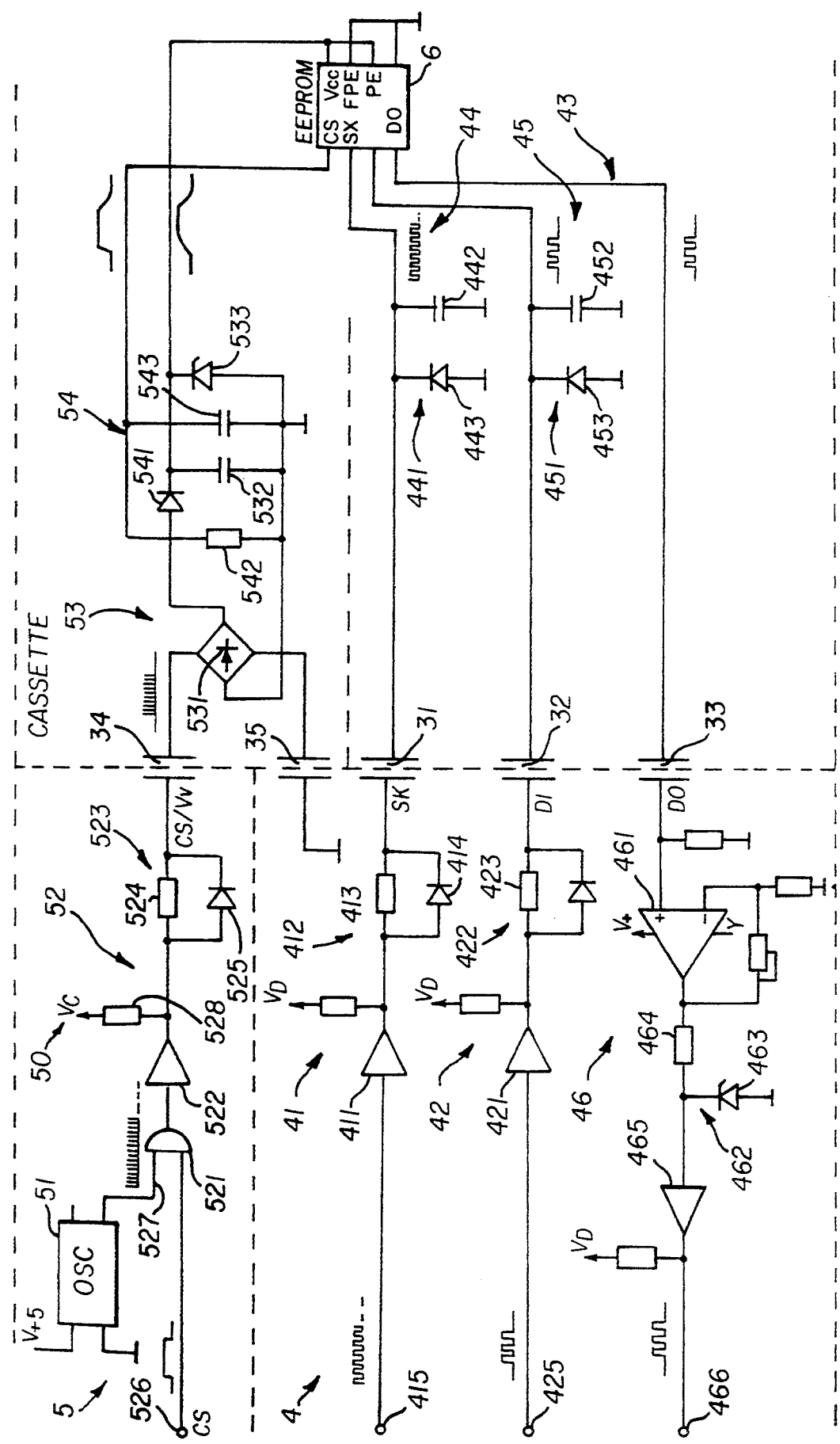
FIG. 3 is a detailed circuit arrangement of the device according to FIG. 2.

As shown in FIG. 3, the signal transmitter circuits 41 and 42 are identically designed and each consists of a signal amplifier 411,421 and a protective circuit 412,422 arranged at the output and each comprising a resistor 413,423 and a diode 414,424 connected in parallel thereto. As shown in FIG. 2, the signal inputs 415 and 425 of the signal amplifiers 411 and 421 are connected to the CPU 40 for radio-frequency signals, and the signal outputs of the protective circuits are connected to the capacitive coupling interfaces 31 and 32 of the coupling device 3.

Via its signal output, the signal transmitter circuit 43 which in this embodiment according to the invention is part of the memory 6 is connected to a coupling interface 33.

At its input which is connected to a coupling element 34, the signal receiver circuit 46 is provided with a first signal amplifier 461, and at its output 466 connected to the CPU 40, it features a second signal amplifier 465, a protective circuit 462 being arranged therebetween having a Zener diode 463 and a resistor 464.

At their outputs connected to coupling interfaces 31 and 32, the signal receiver circuits 44 and 45 which in this embodiment are also part of the memory 6 each comprise a protective circuit 441 and 451 with a capacitor 442 and 452 and a diode 443 and 453 to suppress interfering pulses of undesired polarity and magnitude.

The energy transmitter circuit 52 comprises a gate 521, an amplifier circuit 522 and a protective circuit 523 having a resistor 524 and a diode 525. A first signal input 526 of the gate circuit is connected to the CPU 40 and a second signal input 527 to oscillator circuit 51. The output of the following amplifier circuit 522 is connected via a resistor 528 to power unit 50 and via protective circuit 523 to a coupling interface 34.

The energy receiver circuit 53 for the memory 6 whose input is connected to coupling interface 34 comprises a rectifier circuit 531, a filtering means 532 and a voltage stabilizing means 533.

A further connection to a coupling interface 35 leads to chassis ground.

Via its signal input, the separating circuit 54 consisting of a diode 541, a resistor 542 and a capacitor 543 is connected to the output of the rectifier circuit 531 and via its signal output it is connected to memory 6.

Figure 4:
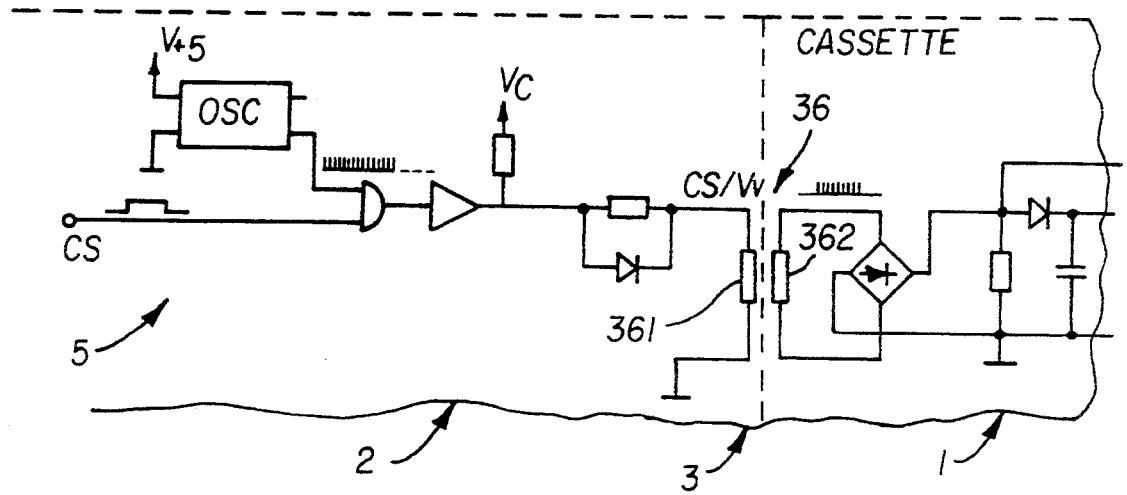
FIG. 4 shows a section of a further embodiment of the device according to FIG. 3.

A further embodiment according to FIG. 4 shows, by way of example for all other coupling interfaces, an inductive coupling interface 36 of the coupling device 3 for the power source 5.

The inductive coupling interface 36 consists of a first induction coil 361 on the side of the cassette identification apparatus 2, and of a second induction coil 362 on the side of cassette 1, the induction coils having an inductivity "L" and dimensions adapted to the radio frequency selected and to the energy to be transferred.

Figure 5:
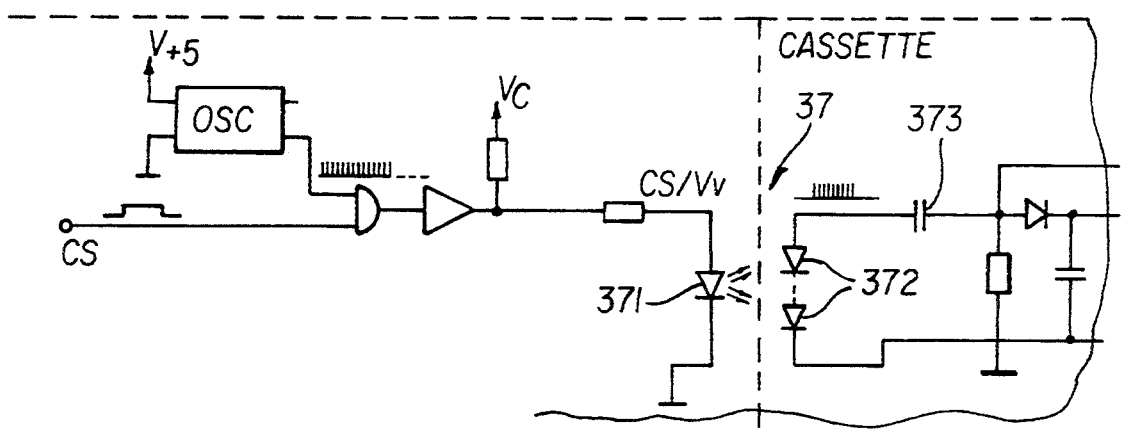
FIG. 5 shows a section of another embodiment of the device according to FIG. 3.

Yet another embodiment according to FIG. 5 shows, also by way of example for all other coupling interfaces, an optoelectric coupling interface 37 of the coupling device 3 for the power source 5. The opto-electric coupling interface 37 consists of an electro-optical transmitter element 371 on the side of the cassette identification apparatus 2, and of a plurality of opto-electric receiver elements 372 and a capacitor 373 on the side of the cassette 1, the transmitter element, the receiver elements and the capacitor being adapted to the radio frequency selected and to the energy to be transferred.

Capacitor 373 is used to suppress steady radiation, e.g. the sunlight, which might cause malfunctions in the memory of a cassette withdrawn from the apparatus.

Figure 6:
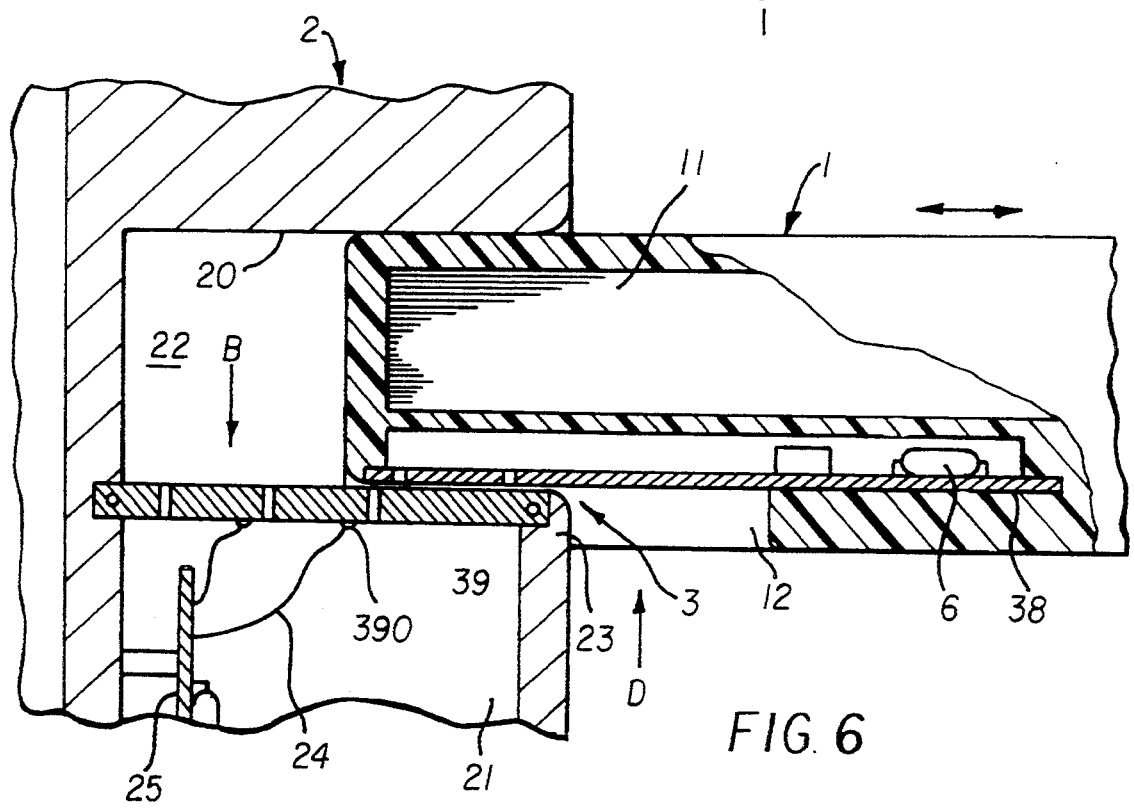
FIG. 6 shows a partial view of a further modified design of the device in a cross-section along the line A—A in FIG. 1.

The design of the device illustrated in FIG. 6 shows the cassette 1 for handling radiation-sensitive recording material 11, the cassette identification apparatus 2 having a feed-in aperture 20 for the cassette and a capacitive coupling device 3, the cassette being shown in a position halfway inserted in the input opening.

The portion of the coupling device 3 designed as a printed circuit board 38 and associated with the cassette 1 is arranged in a marginal area within a recess 12 of the cassette 1 and separated from the recording material. The exposed exterior surface (top view D, FIG. 9) of the end portion of the printed circuit board 38 located in the area of the outer edge of the cassette is provided with the first conductive surfaces of the capacitive coupling interfaces 31 to 35. On the interior surface of the end portion of the PCB 38 extending into the cassette the electrical components of the signal processing unit and its power supply are arranged.

The portion of the coupling device 3 designed as a second PCB 39 and associated with the cassette identification apparatus 2 is arranged within an area 22 of feed-in aperture 20 as a protrusion 23 to fit recess 12 of cassette 1. On its exposed surface (top view B, FIG. 7), the PCB 39 is provided with the second conductive surfaces of the capacitive coupling interfaces 31 to 35 on the interior surface of the PCB 39 facing housing 21, the end connections 24 between the conductors 390 and the PCBs 25 are arranged for the components of the signal processing unit and its power supply.

Figure 8:
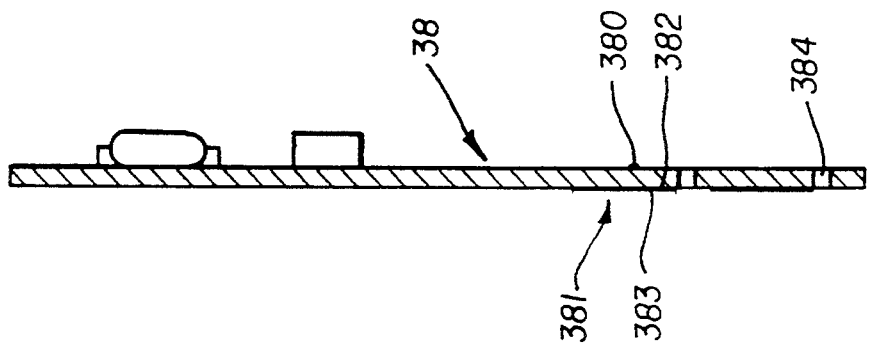
FIG. 8 shows a lateral view of the coupling device in cross-section along a line C—C in FIG. 7.
Figure 7:
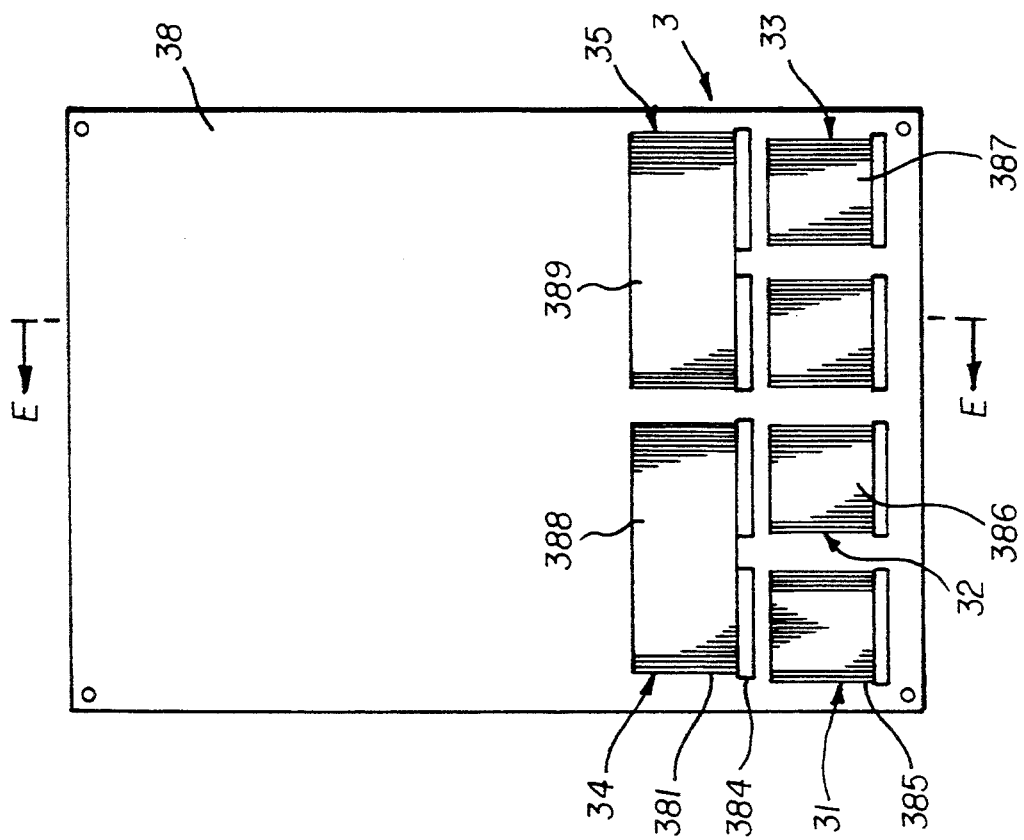
FIG. 7 shows a top view indicated B in FIG. 6 of a coupling device of the cassette identification apparatus used in the device according to the invention.

The PCB 38 of the coupling device 3 located on the side of the cassette and shown in FIGS. 7 and 8 comprises on the illustrated exterior surface two rows of contact elements 385 to 389, the elements 385 to 387 of the lower row being associated with the capacitive coupling interfaces 31 to 33 for the signal transfer, and the elements 388 and 389 of the upper row being associated with the capacitive coupling interfaces 34 and 35 for the energy transfer.

The dimensions of the contact elements 388 and 389 are twice as large as those of the other contact elements. The dimensions of the contact elements are adapted to the energy level and the selected radio-frequency to be transferred and are arranged in a way so as to prevent malfunctions by signal crosstalk.

The contact surfaces of the contact elements are provided with sheet material 381 which are adhered thereto and consist of an aluminum layer 382 and a capacitively conducting layer 383 of plastic material. At the lower edge of the contact elements the sheet material 381 extends through slots 384 to reach the rear side of the PCB 38 in order to be connected to the conductors 380 leading to the electric components and to guarantee protection from the sheet material peeling off when the cassette 1 is inserted in and removed from the feed-in aperture of the cassette identification apparatus 2.

The layer 383 represents a dielectric having a dielectric constant "E", a layer thickness "D" and a surface area "F" whose dimensions are adapted to the energy level and the frequency selected to be transferred. Furthermore, layer 383 has a small coefficient of friction.

Figure 9:
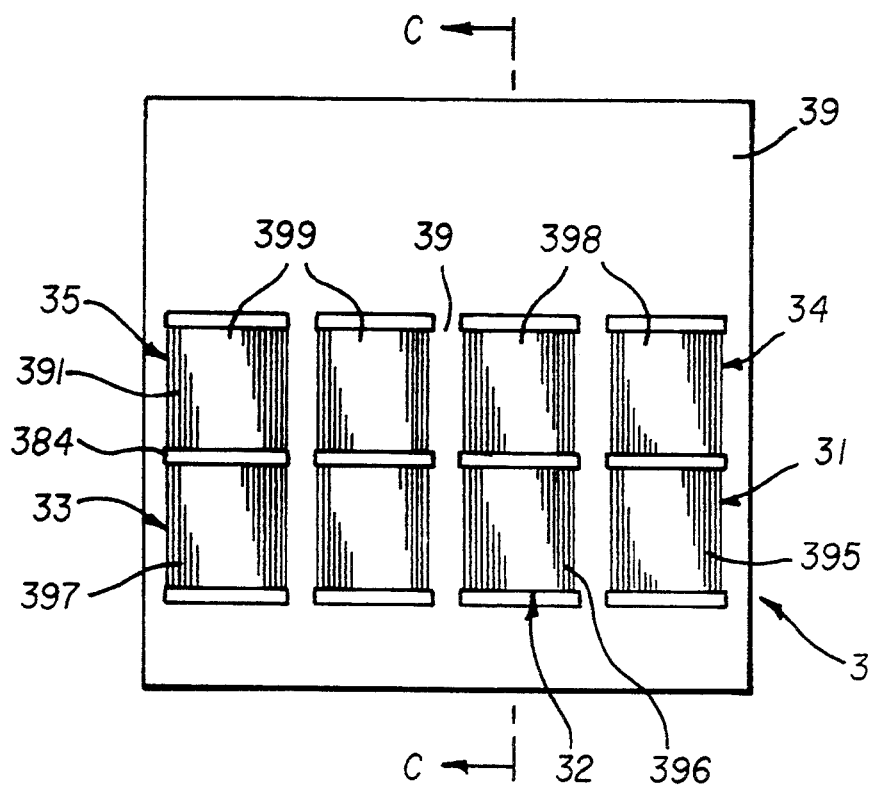
FIG. 9 shows a top view D (FIG. 6) of a coupling device of the cassette used in the device.
Figure 10:
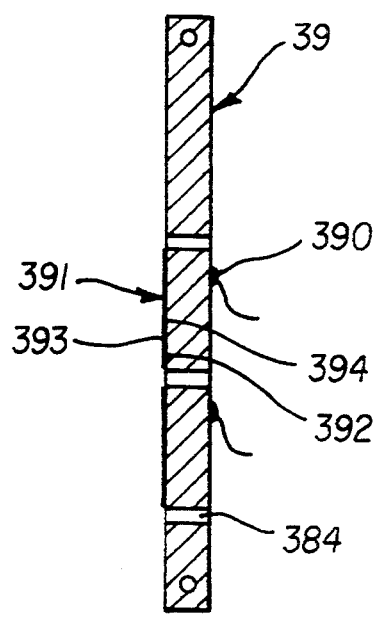
FIG. 10 shows a lateral view of the coupling device in cross-section along a line E—E in FIG. 9.

In contrast to the PCB 38 on the side of the cassette, the PCB 39 of the coupling device 3 located on the side of the apparatus and shown in FIGS. 9 and 10 comprises at each of the coupling elements 395 to 399 of the coupling interfaces 31 to 35 a spring element 394 beneath sheet material 391 consisting of an aluminum layer 392 and an insulating layer 393, in order to guarantee intimate contact of the sheet materials 391 and 381 in the coupling elements when cassette 1 is inserted in feed-in aperture 20 of cassette identification apparatus 2.

The spring element 394 consists of a resilient rubber or plastic film.

The surface areas of the contact elements 398 and 399 are subdivided so as to guarantee the required intimate contact across the entire surface.

The device operates as follows:

As shown in FIG. 1, a cassette 1 containing radiation-sensitive recording material is inserted in feed-in aperture 20 of a cassette identification apparatus 2. In doing so, the contact elements 385 to 389 and 395 to 399 come into contact with one another in the coupling device 3 (as shown in FIGS. 6 to 10) and form the coupling interfaces 31 to 35.

Then the digitized data, e.g. data relating to the patient, the film and/or the cassette, are entered into the memory 6 (or retrieved therefrom and fed to the cassette identification apparatus 2) in a known manner via a keyboard 26, a program software of the cassette identification apparatus 2 or a computer interface 47. Such data can be used by the operator to control the processing of a recording material 11 or to display information on a screen monitor 27 of the cassette identification apparatus 2. Data storage and retrieval in and from the cassette memory as well as the removal of the recording material from cassette 1 are effected in a known way not illustrated.

Transfer of the data to and from cassette 1 and of electric energy to the cassette are effected via the coupling interfaces 31 to 35, and control being effected by means of the microprocessor-controlled CPU 40 shown in FIG. 2.

If a data transfer is to be performed, a control signal "CS" is produced in a generally known manner by means of CPU 40 and fed to signal input 526 shown in FIG. 3 so that for the duration of the signal the gate circuit 521 is opened using the frequency of the oscillator circuit 51 and a radio-frequency supply voltage is produced via the amplifier circuit 522 of the power unit 50.

Via the capacitive coupling interface 34 forming a capacitor, such high frequency supply voltage is transferred to the rectifier circuit 531, the filter means 532 and the stabilizing means 533 and applied to the supply input "Vcc" of the memory 6, which represents an EEPROM.

The control signal "CS" for activating the memory 6 is separated from the rectified supply voltage by means of the signal separating circuit 54 and fed to the input "CS" of the memory. In this case, the control signal "CS" has a steeper signal rise than the supply voltage.

If data are to be stored in memory 6, a radio-frequency control signal "SK", a write cycle, is produced by the CPU 40 and applied to the "SK" input of the memory via the signal input 415, the signal amplifier 411 and the coupling interface 31. At the same time, the CPU 40 feeds data in the form of radio-frequency digital signals to the "DI" input of the memory via the signal input 425, the signal amplifier 421 and the coupling interface 32.

When the data storing procedure is finished, the voltage supply for the memory 6 can be turned off by terminating the control signal "CS" on signal input 526 and the cassette 1 can be removed from the feed-in aperture 20 of the cassette identification apparatus 2 without the stored data getting lost.

If data from memory 6 are to be transferred to the CPU 40, a read cycle is produced by the CPU on signal input 415 and fed to the "SK" input of the memory.

Thereupon, the "DO" output of memory 6 feeds data in the form of radio-frequency digital signals to the signal output 466 and, thus, to CPU 40 via coupling interface 33 and the signal amplifiers 461 and 465.

We claim:

1. A high rate digital data transfer device comprising:
    a radiation sensitive recording material processor having a feed in location for receiving a cassette containing radiation sensitive recording material, said processor having a power unit including a source of a supply voltage, an energy transmitter circuit for converting said supply voltage into a radio frequency voltage, and first galvanically insulated coupling interface for transmitting said radio frequency voltage;
    a cassette containing radiation sensitive material, said cassette carrying a digital data memory, an energy receiver circuit for converting a radio frequency voltage into a supply voltage applied to said digital data memory, and a second galvanically insulated coupling interface connected to said energy receiver circuit for receiving a radio frequency voltage;
    wherein stationarily positioning said cassette at said feed in location of said processor, results in coupling of said second coupling interface with said first coupling interface, so as to transfer said radio frequency supply voltage from said processor to said cassette memory.

2. The device of claim 1 wherein said energy transmitter circuit includes an oscillator for producing radio-frequency signals.

3. The device of claim 1 wherein said first and second coupling interfaces are respective opto-electric coupling interfaces.

4. Device according to claim 3, characterized in that the opto-electric coupling interface (37) comprises an electro-optical transmitter element (371) on the processing apparatus (2) and at least one opto-electric receiver element (372) on the cassette (1) or vice-versa.

5. Device according to claim 4, characterized in that the transmitter element and the receiver element are adapted to the radio-frequency and the energy level to be transferred.

6. The device of claim 1 wherein said first and second coupling interfaces are respective inductive coupling interfaces.

7. Device according to claim 6, characterized in that the inductive coupling interface (36) comprises a first induction coil (361) on the processing apparatus (2) and a second induction coil (362) on the cassette (1).

8. Device according to claim 7, characterized in that the induction coils have an inductivity "L" and are dimensioned in accordance with the radio-frequency selected and the energy to be transferred.

9. The device of claim 1 wherein said processor includes a data processing unit including a data processor, a radio frequency data signal transmitter circuit, and a radio frequency data signal receiver circuit connected to said data processor, third and fourth galvanically insulated coupling interfaces respectively coupled to said transmitter circuit and said receiver circuit; and wherein said cassette includes a radio frequency data signal receiver circuit, a radio frequency data signal transmitter circuit and fifth and sixth galvanically insulated coupling interfaces, such that when said cassette is stationarily positioned at said feed in location of said processor, said third and fourth coupling interfaces are coupled with said fifth and sixth coupling interfaces, to effect reciprocal transfer of radio frequency data signals between said data processor and said digital data memory.

10. The device of claim 9 wherein said third, fourth, fifth and sixth coupling interfaces are respective capacitive coupling interfaces.

11. The device of claim 9 wherein said third, fourth, fifth and sixth coupling interfaces are respective inductive coupling interfaces.

12. The device of claim 9 wherein said third, fourth, fifth and sixth coupling interfaces are respective optoelectric coupling interfaces.

13. The device of claim 9 wherein said data processing unit includes a microprocessor controlled central processing unit for controlling data transfer, data processing and supply voltage transfer.

14. The device of claim 9 wherein said transmitter circuits and said receiver circuits are provided with interference protection circuits.

15. The device of claim 1 wherein said energy receiver circuit includes a signal separating circuit for separating a memory control signal from said radio-frequency voltage.

16. The device of claim 1 wherein said energy transmitter circuit and said energy receiver circuit are provided with interference protection circuits.

17. The device of claim 1 wherein said first and second coupling interfaces are respective capacitive coupling interfaces.

18. Device according to claim 17, characterized in that the capacitive coupling interface (31, 32, 33, 34, 35) comprises a capacitively conducting layer (383, 393) between a conductive coupling element (385, 386, 387, 388, 389) of the cassette (1) and a conductive coupling element (395, 396, 397, 398, 399) of the processing apparatus (2).

19. Device according to claim 18, characterized in that the capacitively conducting layer (383, 393) is a dielectric having a dielectric constant "E", a layer thickness "D" and a surface area "F" dimensioned in accordance with the radio-frequency and the energy to be transferred.

20. Device according to claim 18, characterized in that the coupling elements of the cassette (1) and the processing apparatus (2) can be pressed against each other by means of spring elements.

* * * * *